US010932739B2

(12) United States Patent
Florent et al.

(10) Patent No.: US 10,932,739 B2
(45) Date of Patent: Mar. 2, 2021

(54) DYNAMIC NORMALIZATION OF DATA FOR PERFUSION COMPARISON AND QUANTIFICATION

(75) Inventors: Raoul Florent, Ville d'Avray (FR); Cecile Dufour, Paris (FR); Vincent Auvray, Meudon (FR); Odile Bonnefous, Rueil-Malmaison (FR)

(73) Assignee: KONINKLIJKE PHILIPS N.V., Eindhoven (NL)

(*) Notice: Subject to any disclaimer, the term of this patent is extended or adjusted under 35 U.S.C. 154(b) by 438 days.

(21) Appl. No.: 14/004,195

(22) PCT Filed: Feb. 28, 2012

(86) PCT No.: PCT/IB2012/050921
§ 371 (c)(1),
(2), (4) Date: Sep. 10, 2013

(87) PCT Pub. No.: WO2012/127339
PCT Pub. Date: Sep. 27, 2012

(65) Prior Publication Data
US 2014/0005538 A1 Jan. 2, 2014

(30) Foreign Application Priority Data
Mar. 18, 2011 (EP) .................................. 11305304

(51) Int. Cl.
*A61B 6/00* (2006.01)
*G06T 7/00* (2017.01)
(Continued)

(52) U.S. Cl.
CPC .............. *A61B 6/481* (2013.01); *A61B 6/486* (2013.01); *A61B 6/503* (2013.01); *A61B 6/504* (2013.01);
(Continued)

(58) Field of Classification Search
CPC ......... A61B 6/00; A61B 6/507; A61B 6/5217; A61B 6/486; A61B 6/503; A61B 6/583;
(Continued)

(56) References Cited

U.S. PATENT DOCUMENTS

| 4,729,379 A | 3/1988 | Ohe |
| 2004/0082846 A1 | 4/2004 | Johnson et al. |

(Continued)

FOREIGN PATENT DOCUMENTS

WO WO2010018500 2/2010

OTHER PUBLICATIONS

Waechter et al. Model-based blood flow quantification from rotational angiography. 2008 Medical Image Analysis 12:586-602.*
(Continued)

*Primary Examiner* — Keith M Raymond
*Assistant Examiner* — Patrick M Mehl

(57) ABSTRACT

The invention relates to x-ray imaging technology as well as image post-processing. Particularly, the present invention relates to post-processing of perfusion image data acquired by an x-ray imaging apparatus by absolutely or relatively normalizing perfusion image data to allow a preferred comparison of the image data, both with regard to different acquisitions as well as different patients. To allow normalization of perfusion image data, it may be desirable to know the amount of contrast agent injected, which remains in a coronary. Subsequently, image parameters may be adapted or normalized based on the known amount of contrast agent within the coronary for normalization of perfusion image data. To obtain a precise amount of injected contrast agent, the injected volume of contrast agent flowing through a defined region or section of a vessel may be estimated. Said injected volume of contrast agent may thus be deduced from the estimation of the total volume flow at this location.

(Continued)

Accordingly, a method (10) is provided for dynamic normalization of data for perfusion comparison and quantification, comprising the steps of determining (20) a total volume flow or an amount of a contrast agent in a blood vessel and normalizing (34) perfusion data based on the determined total volume flow or amount of contrast agent.

19 Claims, 4 Drawing Sheets

(51) Int. Cl.
  *A61B 6/12* (2006.01)
  *G06T 5/50* (2006.01)
  *G06T 5/00* (2006.01)
(52) U.S. Cl.
  CPC ............ *A61B 6/507* (2013.01); *A61B 6/5217* (2013.01); *G06T 5/008* (2013.01); *G06T 5/50* (2013.01); *G06T 7/0012* (2013.01); *A61B 6/12* (2013.01); *A61B 6/4441* (2013.01); *A61B 6/464* (2013.01); *A61B 6/5235* (2013.01); *A61B 6/583* (2013.01); *G06T 2207/10116* (2013.01); *G06T 2207/30104* (2013.01)
(58) Field of Classification Search
  CPC ......... A61B 6/12; A61B 6/464; A61B 6/5235; A61B 6/4441; A61B 6/481; A61B 6/504; G06T 5/008; G06T 5/50; G06T 7/0012; G06T 2207/30104; G06T 2207/10116
  USPC .................................. 600/431; 382/131, 130
  See application file for complete search history.

(56) References Cited

U.S. PATENT DOCUMENTS

| 2008/0292049 | A1 | 11/2008 | Camus et al. | |
| 2009/0116715 | A1* | 5/2009 | Bredno | A61B 6/481 382/130 |
| 2009/0274358 | A1* | 11/2009 | Flohr | A61B 6/032 382/131 |
| 2010/0208971 | A1 | 8/2010 | Neukirchen et al. | |

OTHER PUBLICATIONS

Yoganathan et al. Review of hydrodynamic principles for the cardiologist Applications to the study of blood flow and jets by imaging techniques. 1988 J.Am.College of Cardiology 12:1344-1353.*

Hawkes et al. Development of a model to predict the potential accuracy of vessel blood flow measurements from dynamic angiographic recordings. 1988 in Mathematics and Computer Science in Medical Imaging—NATO ASI Series F39 Springer-Verlag pp. 469-478.*

Hayashi et al. New measurement of hepatic blood flow by Xenon CT system : An animal study with PGE1. 2005 J.Surg.Res. 129:24-30.*

Kapoor.Techniques of cardiac catheterization and coronary angiography. In "Interventional Cardiology", Kapoor AS (ed), Springer-Verlag, 1989 Chap. 2 p. 10-21.*

Van't Hof et al. Angiographic assessment of myocardial reperfusion in patients treated with primary angioplasty for acute myocardial infarction. Myocadial blush grade. 1998 Circulation 97:2302-2306.*

Korporaal et al. 2011 Proc. Intl. Soc. Mag. Reson. Med. 19: oral presentation at the Third Annual Meeting of the ISMRM Benelux Chapter Jan. 19, 2011 Hoeven Netherlands, 1 page (Year: 2011).*

J. Waechter et al., "Model-based blood flow quantification from rotational angiography"; Medical Image Analysis, vol. 12, issue 5, pp. 586-602 (Oct. 2008).

J.R. Linder et al., "Myocardial Perfusion Characteristics and Hemodynamic Profile of MRX-115, a Venous Echocardiographic Contrast Agent, During Acute Myocardial infarction", Journal of the American Society of Echocardiography, Mosby-Year Book, Inc. St. Louis, MO, US, vol. 11, No. 1, Jan. 1, 1998, pp. 36-46.

T. Bolke et al., "Phantom Based Flow Analysis by Means of Dynamic Angiography, CFD and Laser-Doppler-Velocimetry", Nuclear Science Symposium Conference Record, 2007, NSS 2007, IEEE, PI, Oct. 1, 2007, pp. 3440-3445.

Sekiguchi, "Image Processing on Regular Coronary Angiograms for Myocardial Perfusion Measurements", Computers Cardiology, vol. 33, 2006, Pages. pp. 821-824.

Gatta et al, "Towards Robust Myocardial Blush Grade Estimation on Contrast Angiography" Computer Science; vol. 5524 Image Analysis and Processing , 2009 pp. 249-256.

Bredno et al, "Algorithmic Solutions for Live Device-to-Vessel Match", Proceedings of SPIE; vol. 5370; 2004, pp. 1486-1497.

Xu et al., "Simulation of Contrast Agent Transport in Arteries with Multilayer Arterial Wall: Impact of Arterial Transmural Transport on the Bolus Delay and Dispersion", Scientific World Journal, vol. 2014 (2014).

Caille, Jean-Marie et al "Variations in the Measurement of Regional Cerebral Blood Volume by Cat", Computerized Medical Imaging and Graphics, vol. 2, Issue 2, 1978, Abstract Only.

Hu, Xiao-yun, "Pulmonary Perfusion Imaging with 64-Slice CT in Radiation-Induced Lung Injury (RILI): Primary Clinical Study", 2008.

Cusma, Jack T. et al, Digital Subtraction Angiographic Imaging of Coronary Flow Reserve, Circulation, 1987, vol. 75, No. 2, pp. 461-472.

* cited by examiner

DYNAMIC NORMALIZATION OF DATA FOR PERFUSION COMPARISON AND QUANTIFICATION

CROSS-REFERENCE TO PRIOR APPLICATIONS

This application is the U.S. National Phase application under 35 U.S.C. § 371 of International Application Serial No. PCT/IB2012/050921, filed on Feb. 28, 2012, which claims the benefit of European Application Serial No. 11305304.5, filed on Mar. 18, 2011. These applications are hereby incorporated by reference herein.

FIELD OF THE INVENTION

The invention relates to x-ray imaging technology as well as image post-processing.

In particular, the present invention relates to a method and an apparatus for dynamic normalization of data for perfusion comparison and quantification, a computer-readable medium, a program element as well as a processing device.

Particularly, the present invention relates to post-processing of perfusion image data acquired by an x-ray imaging apparatus by absolutely or relatively normalizing perfusion image data to allow a preferred comparison of the image data, both with regard to different acquisitions as well as different patients.

BACKGROUND OF THE INVENTION

Nowadays, a common surgical procedure is the so-called percutaneous coronary intervention or PCI. During this intervention, a catheter is inserted into the vascular system of a patient at an access site. The catheter is advanced along respectively within large vessels to a particular vascular structure, which requires treatment.

Contrast agent is subsequently injected via the catheter and an x-ray imaging apparatus is employed for acquiring an angiographic image sequence showing the vessel structure when being filled with contrast agent.

Regularly, a two-dimensional image data is obtained, e.g. by a C-arm x-ray imaging apparatus. In other embodiments, also three-dimensional medical imaging modalities may be employed for obtaining a three-dimensional vessel structure.

The so obtained angiographic image data is provided to a physician and is subsequently employed for planning of an intervention procedure. However, not only coronary angiogram data is of interest to a physician but also information regarding the myocardial perfusion.

Here, perfusion is defined as the passage of fluid through a lymphatic system or blood vessels up to and into an organ or tissue. Perfusion scanning is thus the process by which the perfusion can be observed, recorded and quantified.

E.g., patients with heavy cardiac diseases ordinarily undergo cardiac catheterization. In the course of such a procedure, the degree of a coronary stenosis and/or an aneurysm size may be determined.

However, information regarding myocardial perfusion may not be obtained from the coronary shape alone as provided by a coronary angiogram. This may e.g. be because once a stenosis occurs, the remaining normal coronary vessel structure may begin to provide the ischemic muscle with blood, resulting in scarcely any relation between the coronary shape and myocardial perfusion.

During acquisition of coronary angiogram image data, also myocardial perfusion image data may be obtained.

For improving visibility of myocardial perfusion image data, e.g. background features or image parts that do not belong to either the coronary angiogram or the myocardial perfusion data per-se may be subtracted, e.g. removed, from the images acquired, thus resulting in images where only the injected coronaries and the myocardial perfusion are visible.

Such a process is known in the art as a DSA process. E.g., in order to examine a patient's heart, mask images corresponding to one cardiac cycle may be acquired before injection of a contrast agent and subsequently subtracted from the image data acquired during a coronary angiogram. This subtraction is performed between the mask images and the contrast images relating to the same cardiac beat phase, thereby removing image components due to the cardiac beat from the subtraction images.

US 2004/0082846 A1 describes a method and apparatus for volumetric cardiac computed tomography scanning for estimating a density of contrast agent in a selected region.

SUMMARY OF THE INVENTION

One object of the present invention may be seen in providing a preferred means for analyzing, interpreting and quantifying perfusion image data.

This object may be achieved by the subject-matter of the independent claims. Preferred embodiments of the present invention are described in the dependent claims.

The comparison or quantification of myocardial perfusion image data in cardiac angiography, e.g. before and after a stenting procedure, may be considered to be complex because the amount of contrast agent injected in the coronaries is difficult to control. In particular the backflow leakage of contrast agent from the coronaries back into the aorta may not be neglectable.

The large volume of blood pumped into the aorta indeed creates a pressure difference, which tends to suck part of the contrast agent that was injected through the corresponding coronary ostium via an injection catheter back into the aorta. This natural phenomenon has to be accounted for to allow a meaningful comparison of perfusion image data or even quantification within the myocardium with regard to different image acquisitions or even different patients.

While further measures during contrast agent injection are known, e.g. ECG gated injection with controlled amount, dilution rate and injection rate, the impact of contrast agent backflow into the aorta may still have to be considered. When comparing perfusion situations, even a slight modification in a considered grey level scaling of image information may provide huge differences in a situation assessment.

This may even hold more true when comparing perfusion situations in which the coronary structure has been altered, e.g. before and after a stenting procedure, due to vastly differing perfusion parameters due to an altered coronary vessel structure.

The aspects, features and advantages of the present invention may further be derived from the detailed description of preferred embodiments described hereinafter, which are explained with reference to the following drawings.

Like elements may be referred to with like reference numerals.

The figures are not drawn to scale, however may depict qualitative proportions.

DETAILED DESCRIPTION OF PREFERRED EMBODIMENTS

Figure 1:
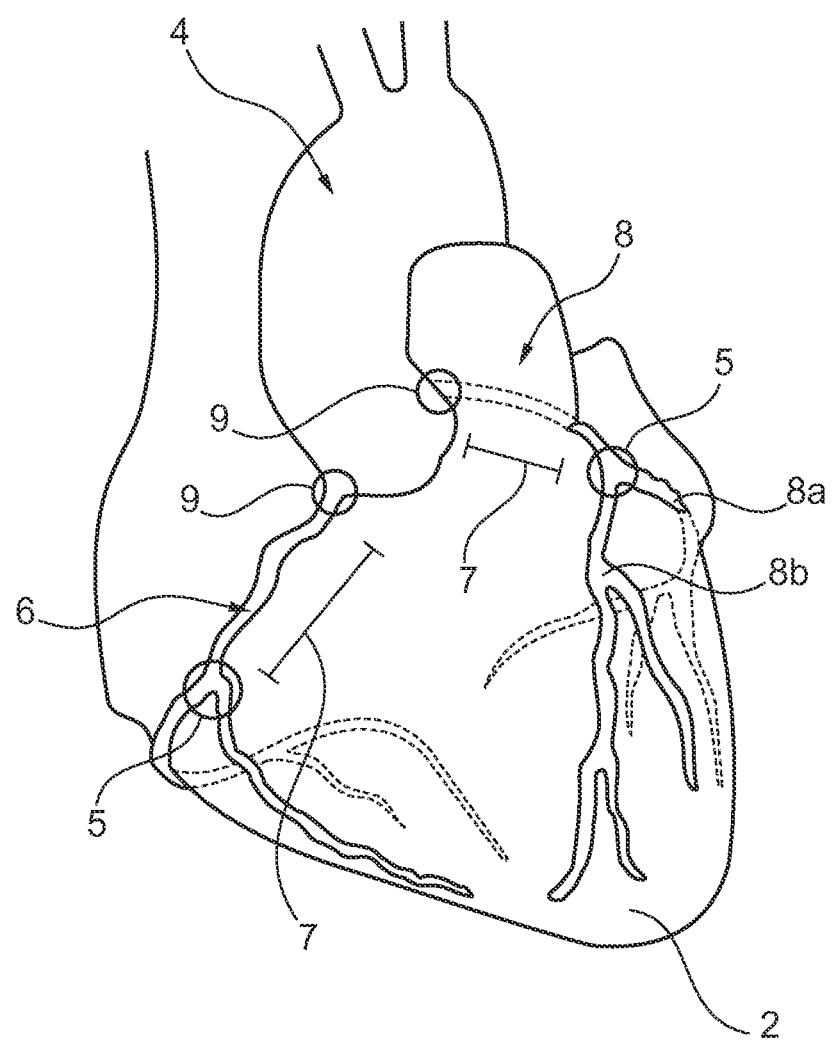
FIG. 1 shows a schematic representation of a vessel structure of a myocardium.

To allow normalization of perfusion image data, it may be desirable to know the amount of contrast agent injected, which remains in a coronary. Subsequently, image parameters may be adapted based on the known amount of contrast agent within the coronary for normalization of perfusion image data.

To obtain a precise amount of injected contrast agent, the injected volume of contrast agent flowing through a defined region or section of a vessel may be estimated. Said injected volume of contrast agent may thus be deduced from the estimation of the total volume flow at this location.

E.g. during an angiographic procedure, the tip of the injection catheter may be tracked on live acquired x-ray images. The tip of the injection catheter may subsequently be introduced into a coronary artery for injection of contrast agent. The tip of the injection catheter may subsequently be arranged in a part of a respective coronary artery, which is substantially bifurcation-free, e.g. embodied as a single blood vessel with a defined geometrical structure. Said part of a coronary artery is subsequently referred to as the main collector, so exemplifying a section or region within the coronary artery into which the contrast agent is injected.

Regularly, the catheter tip is not introduced into the coronary artery far beyond the coronary ostium so that the injection of contrast agent also takes place at the main collector being arranged in the vicinity of the respective coronary ostium.

When now injecting contrast agent into the coronary artery, the main part of contrast agent is flowing through the coronary towards the myocardial tissue structure, while a small, however non-neglectable, amount of contrast agent may be considered to be leaking back into the aorta due to the backflow effect. For precisely obtaining normalized perfusion image data it is thus required to precisely know or estimate that part or amount of contrast agent that is flowing through the main collector, remaining in the respective coronary artery, so contributing to the acquisition of myocardial perfusion image data.

Due to the substantial blood flow in the aorta, that part of the contrast agent that is leaking back into the aorta is of no contribution at all to a localized perfusion image and may thus be completely neglectable.

Though an injected amount of contrast agent may be known to a certain accurate degree, the aforementioned aortic backflow requires an updated determination of contrast agent amount.

To obtain the precise amount of contrast agent flowing through the main collector, the present invention proposes to estimate the integrated volume of contrast agent flowing through the main collector. This estimation, probably up to a multiplicative term, may subsequently be used to normalize perfusion image data over the full image run, allowing proper quantification or comparison of perfusion image data.

In case the geometric parameters of a vessel structure are known, an absolute value may be obtainable, allowing an absolute normalization. In case the vessel structure is not precisely known, at least a relative value of contrast agent is obtainable, at least allowing a relative normalization.

However, only when comparing different patients, absolute values may be required, since with the same patient any multiplicative term would be present identically in each individual acquisition procedure and would thus be cancelling itself out with regard to different image acquisitions.

The proposed method allows getting comparable results even if a variable amount of contrast agent actually flows through the myocardium, in particular due to the backflow phenomenon.

However, ECG triggered and controlled injection may still be taken into account when administering contrast agent via the tip of the injection catheter into the coronary vessel.

The estimation of the injected volume of contrast agent flowing through the main collector may be deduced from the estimation of the total volume flow at this location.

Another possible discrepancy between the two stages of a perfusion comparison might come from the different blood speeds occurring during those stages. For instance, before and after coronary repair (stenting), the blood flows might differ due to the modified vessel shapes at the stenosis location. Now, since perfusion is observed through opacification, and since higher blood flow implies a lesser opacification due to higher dilution, any flow discrepancy might potentially lead to a perfusion assessment discrepancy. The same applies if the contrast is injected at a different speed. But in both cases, measuring the blood volume flow along time in the main collector enables normalisation of the two situations.

A few considerations during the image acquisition procedure may be beneficial for a subsequent normalization procedure.

While a normalization based on an estimation of an injected volume of contrast agent flowing through the main collector may allow the cancellation of differences in image data resulting from said differing contrast agent volume or contrast agent amount, it may be beneficial to also control the acquisition parameters of an x-ray imaging system to closely match between different image acquisition procedures and possibly even between different patients. In other words, specific acquisition settings might be useful for perfusion quantification and/or comparison. E.g. it may be beneficial to switch off a continuous automatic dose control of an image acquisition system, at least in order to get a proper digital subtract image result.

Also, employing the same or comparable system settings or image acquisition parameters of an x-ray imaging system during acquisition of different perfusion data sets, e.g. for a pre-/post-stenting comparison may be beneficial.

Further, to provide an adequate basis for a subsequent contrast agent volume estimation, the injection procedure of contrast agent into the main collector may be precisely controlled for allowing a fine perfusion analysis. Such a controlled injection may include triggering the injection with the or depending on specific cardiac cycles, i.e. ECG triggered, and further controlling the injection amount, the dilution or ratio of total vessel volume versus contrast agent volume as well as the injection speed.

To obtain a meaningful result of perfusion image data, the aforementioned masking may be required so that only the coronary angiogram image data with subsequent perfusion image data remains. In other words, the input data, which may be the injected angiogram, should contain a pre-injection phase, which may be used for masking purposes and the per se injection phase.

During the pre-injection phase, ECG triggered or ECG dependent images may have been acquired, which are subsequently employed for masking purposes of non-relevant tissue structures in the obtained perfusion image data. Both phases, the pre-injection phase and the per se injection phase shall be compatible with the subsequent cardiac DSA process, which is well-known in the art.

For a preferred administering of contrast agent in the main collector, the catheter tip or the injection tip may be tracked along the input sequence until properly located, e.g. by live x-ray images. The injection tip tracking process may be assisted by employing known image processing segmentation and tracking tools. Well-identifiable characteristics of the injection tip, e.g. a contrasted tube of known section, may ease this optional step, which primarily facilitates the main collector tracking.

Here, the main vessel collector, a section or region of a vessel just after the ostium, located at the output of the injection tip is tracked. For the main vessel collector, only a short segment may be required. This vessel segment shall not contain a sizable bifurcation. With regard to the coronary arteries, for the left coronary tree, the collector may be what is known as the "left main". For the right coronary tree, the main vessel collector may e.g. be the vessel stump, which emerges from the aorta.

This step may be greatly facilitated by the result of the injection tip tracking step, since the main collector may be considered to lie in the alignment of the injection catheter.

Neurology intervention is another situation where the present invention might be applied. The perfusion is assessed in the brain after contrast injection. Again, measuring the blood volume flow along time and at the injection point, or at any point upstream to the local observed area, may be necessary for proper perfusion comparison. One can even apply the same principle to normalise the measurement of contrast activity within an aneurysm, typically before and after flow-diverter implantation. Whereas the contrast activity in the aneurysm cavity is not precisely a perfusion effect, from a broader perspective, the same principle can be applied. One might extent the perfusion concept to the study of the contrast opacification in an area distal to a feeding point.

At this point in the image acquisition procedure, pre-injection phase images may have been acquired, in particular ECG dependent images. Now, the injection of contrast agent may be commenced.

The angiographic images acquired after the injection of contrast agent may be processed in a so-called cardiac DSA process. In this step, cardiac DSA is achieved. Said cardiac DSA process may be seen to amount to finding, for each current injected frame or image, a non-injected frame from the pre-injection phase images, which may be employed for subtracting so as to remove background image information, leaving only the contrast agent contribution. In a non-cardiac case, for instance in neurology, DSA often simply amounts to a mere subtraction between a contrast-free image (the mask) and a currently contrast-injected image series. The non-injected images may be required to be geometrically warped for a possible motion compensation for a preferred subtraction and removal of background image signals. Thus possibly, motion induced artefacts may remain in a DSA processed image besides the contrast agent contribution in a respective coronary artery.

Next, as a central aspect of the present invention, the integrated contrast agent volume estimation or contrast agent amount estimation over time is performed, actually realized in several steps. More generally, normalization is performed through the estimation of the total volume flow along time.

First, a total volume flow estimation is performed. The total volume flow within the main collector relates to the volume flow of the total fluid, both blood and contrast agent. Said total fluid flow is estimated over a defined, fine section or cross-section of the main collector in the DSA images.

For total volume flow estimation, several methods are known in the art (e.g. J. Waechter, J. Bredno, P M J Rongen, J. Weese, D. C. Barratt, D. J. Hawkes: Model-based blood flow quantification from rotational angiography"; Medical Image Analysis, vol. 12, issue 5, pages 586-602 (October 2008), the disclosure of which is incorporated herein by reference).

Also, the total volume flow may be estimated or determined by a locally arranged flowmeter within the main collector.

The total volume flow estimation may be an absolute estimation or volume flow may be estimated at least up to a multiplicative factor $\varphi$. In the latter case, the foreshortening and diameter of the main collector, i.e. the geometrical properties of the vessel structure, may not have to be known or estimated.

This total volume flow estimation may either provide the total absolute volume flow $q_T(t)$ or the relative total volume flow $q'_T(t)$, which relate to one another according to equation 1.

$$q'_T(t) = \varphi q_T(t) \qquad \text{Equation 1}$$

Subsequently, as a next step, the contrast flow is measured over the same fine section of the main collector, seen in projection, and over a unit time sample. This value is subsequently referred to as C(t) at a time t. For obtaining C(t), the volume flow of the injected contrast agent is considered. Injected contrast agent refers to only that part of the contrast agent that remains in the respective vessel and is not leaking back into the aorta, i.e. that part flowing through the main collector.

Optimally, the image acquisition system is calibrated so leading to a constant or multiplicative factor $\alpha$, which relates the observed contrast, i.e. the observed image contrast, to a specific absorption level. The constant $\alpha$ may also depend on the nature of the contrast agent employed and on its proper dilution.

Accordingly, an observed image contrast relating to a specific absorption level, taking into account $\alpha$ allows the subsequent determination of the volume flow of the injected contrast agent into the main collector. Thus, observed image contrast C(t) may be determined by equation 2.

$$C(t) = \alpha \cdot \frac{q_I(t)}{q_T(t)} \qquad \text{Equation 2}$$

$q_I(t)$ relates to the volume flow of the injected contrast agent in the main collector, while the ratio of $$\frac{q_I(t)}{q_T(t)}$$

relates to the dilution of contrast agent and therefore, is directly related to the observed absorption level in the image.

Alpha is determined from system calibration and contrast agent type. System calibration simply means that a defined physical absorption may be related to a defined gray level. It is assumed that this may be achieved by only a multiplication factor, but offsets might also intervene. Such a calibration may be accurately performed using known absorption phantoms or test patterns.

C(t) is the observed contrast or, equivalently, the observed gray level value in the background-removed DSA image that varies in time according to the ratio of the injected and total flows. E.g., if the total flow is suddenly growing by a factor 10 with respect to the injected flow, the observed contrast will simply decrease by a factor of 10. Thus, the ratio is the dilution factor of the contrast agent in the blood.

Subsequently, the quantity of the injected contrast agent in the myocardium is determined over time by a contrast agent volume integration, from the starting injection time $t_0$ to current time t. The estimation over time is of particular importance, since it is required to normalize throughout the sequence.

The volume and thus the amount may either be obtained up to a multiplicative term, so resulting in $Q'_I(t)$ or in absolute value $Q_I(t)$. The respective determination is employing either equation 3a or 3b.

$$Q_I(t) = \int_{t_0}^{t} q_I(t)\,dt = \frac{1}{\alpha} \cdot \int_{t_0}^{t} q_T(t) \cdot C(t)\,dt \qquad \text{Equation 3a}$$

$$Q'_I(t) = \int_{t_0}^{t} q'_T(t) \cdot C(t)\,dt \qquad \text{Equation 3b}$$

After obtaining the contrast agent volume integration information and thus the quantity of the injected contrast agent, a data normalization process is conducted. Here, the quantities $Q_I(t)$ or $Q'_I(t)$ may be employed for normalizing the current image data D(t), corresponding to the DSA image information at time t.

A relative normalization between two data sets $D_1(t)$ and $D_2(t)$, e.g. for comparing a pre-stenting scenario with a post-stenting scenario may be achieved by equations 4A and 4B, so obtaining comparable image information.

$$\frac{D_1(t)}{Q'_{I1}(t)} \text{ comparable to } \frac{D_2(t)}{Q'_{I2}(t)} \qquad \text{Equation 4a,b}$$

An according relative normalization for comparison may be sufficient when considering the same patient.

For considering and comparing different patients or for a real quantification, an absolute normalization may be required according to equation 5.

$$\frac{D(t)}{Q_I(t)} \qquad \text{Equation 5}$$

In practice, D(t) often refers to the peak opacification (POP), which may typically be used for perfusion assessment. At every pixel x, the contrast is estimated over the considered sample time t. For instance, in cardiac applications, one typically defines one sample every heart beat for a given cardiac phase, whereas in neuro applications, the sampling rate may be defined and in particular correspond to the actual frame rate. This defines a contrast image sequence C(x, t) and the peak opacification image is defined in accordance with equation 6.

$$POP(x) = \max_{t} C(x, t) \qquad \text{Equation 6}$$

Now, the normalisation scheme may be considered to consist of incorporate the normalisation factor, which may be considered to be pixel independent, since defined only at the main collector level as, into this maximum computing by employing equation 7.

$$NormPOP(x) = \max_{t} \frac{C(x, t)}{Q_I(t)} \qquad \text{Equation 7}$$

The peak opacification indicator may not be the only means to assess perfusion, but the same kind of reasoning may be applied to the perfusion normalisation in general.

A subsequent visualization, comparison or quantification may be performed by employing usual quantification or comparison means, e.g. side by side colour based blush representation. In case of an absolute normalization, absolute quantification figures/values may be computed and displayed, irrespective of the exact injection conditions.

The invention is described by features described in relation to a method for dynamic normalization of data for perfusion comparison and quantification, an apparatus, a computer readable medium, a program element, a processing device and a method for operating a device. However, it is to be understood that the features are not to be considered exclusively relating to a specific category but are interchangeable and indeed may be employed in each of the respective categories of a method for dynamic normalization of data for perfusion comparison and quantification, an apparatus, a computer readable medium, a program element, a processing device and a method for operating a device.

Now referring to FIG. 1, a schematic representation of a vessel structure of a myocardium is depicted.

FIG. 1 shows a schematic representation of myocardium 2. Aorta 4 is depicted from where the right coronary artery 6 as well as the left coronary artery 8 extend. The respective coronary arteries 6,8 have a coronary ostium 9 at the entrance from aorta 4 into the respective coronary artery 6, 8. Left coronary artery 8 subsequently divides into the circumflex artery 8a and the left anterior descending artery 8b.

The sections of the respective coronary arteries 6,8 between each ostium 9 and the respective first bifurcation 5 may be referred to as the main coronary collector 7. From said coronary collector 7, only a small defined section or cross-section is employed for the method according to the present invention, in particular the total volume flow estimation.

During an angiogram procedure, regularly only one of the coronary arteries 6,8 is imaged at any one time, since contrast agent may only be injected in one of the coronary arteries 6,8 at a specific time. After the DSA process only the vessel structure of the respective coronary artery 6,8 remains in the perfusion image, since the DSA process shall ensure, that non-relevant information, e.g. the cardiac muscle tissue as well as the aorta, is removed from the image.

Now referring to FIGS. 2a to d, exemplary embodiments of coronary perfusion images are depicted. These figures correspond to the Peak Opacification (POP) visualisation for a given cardiac phase.

FIGS. 2a to d exemplify the difficulties when not employing a normalization procedure.

Figure 2A:
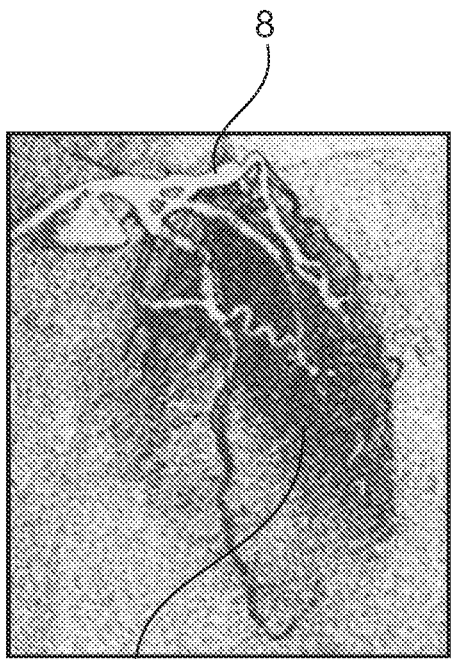
FIGS. 2a-d show exemplary embodiments of coronary angiograms.
Figure 2B:
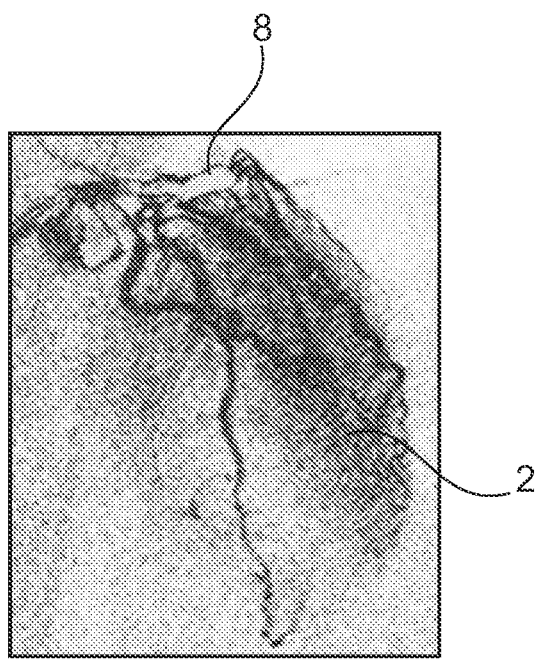

With regard to FIGS. 2a,b, both figures refer to substantially the same present case, possibly even to identical image data, however FIGS. 2a and 2b are depicted with a different scaling or different reference peak opacification value, so resulting in a substantially different depiction of the identical anatomical situation. Indeed, the imaged left coronary artery 8 is not depicted to the same extend in FIGS. 2a,b. Thus, without normalization, a meaningful comparison between FIGS. 2a and 2b is thus not feasible.

Figure 2C:
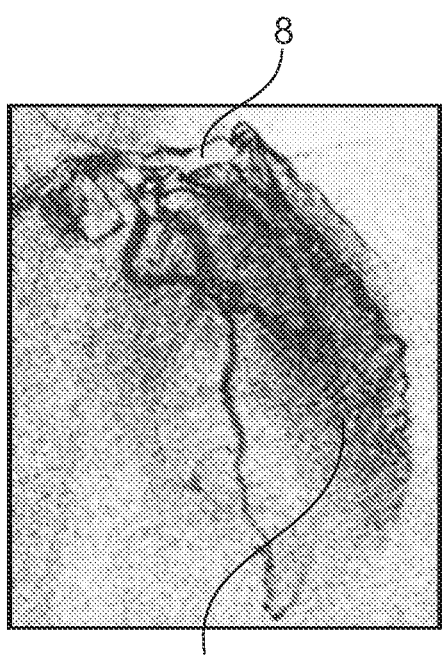
Figure 2D:
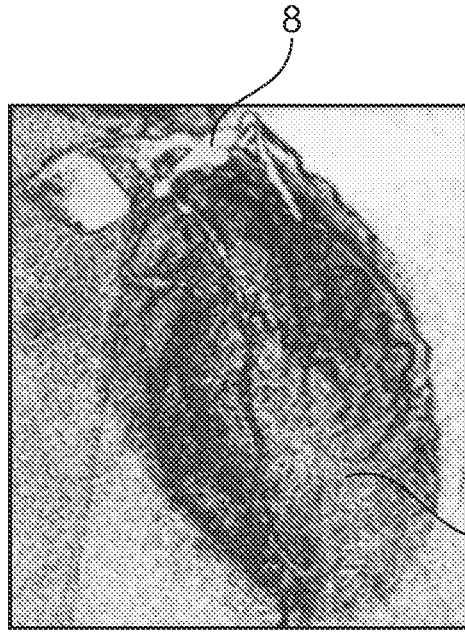

With regard to FIGS. 2c and 2d, FIG. 2c shows a pre-stenting perfusion scenario while FIG. 2d is showing the respective associated post-stenting scenario.

The reference values or the scaling may have been adjusted manually with respect to FIGS. 2c and 2d, so permitting a meaningful comparison of the anatomical situation pre- and post-stenting.

By employing the normalization method according to the present invention, the manual adjustment of the scaling may not be required any more. Rather, directly comparable image information or cardiac perfusion image data is obtainable. Exemplarily, FIGS. 2a to 2d show a scenario of the left coronary artery.

Figure 3:
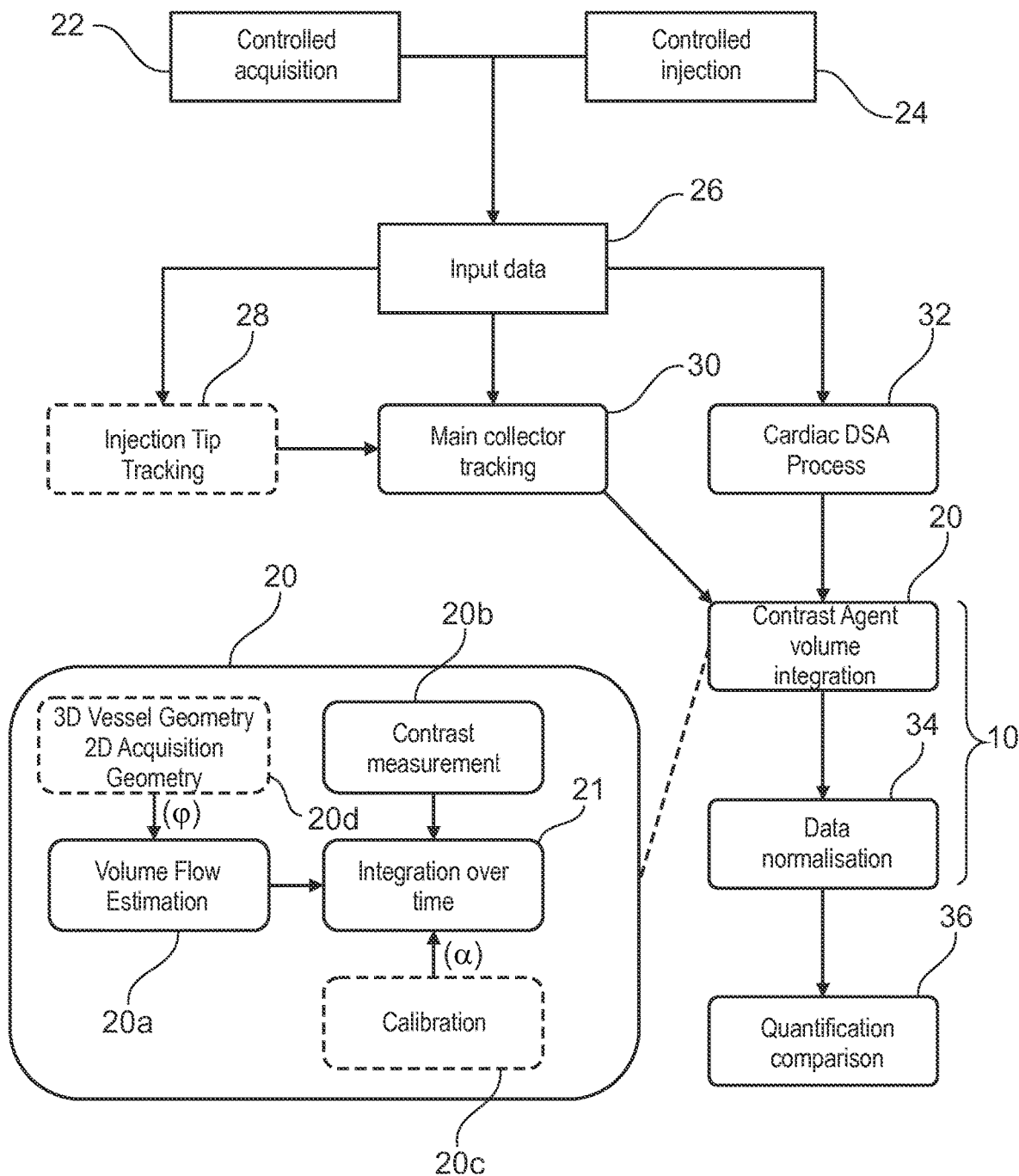
FIG. 3 shows an exemplary embodiment of a method for dynamic normalization of perfusion data for comparison and quantification according to the present invention.

Now referring to FIG. 3, an exemplary embodiment of a method for dynamic normalization for cardiac perfusion comparison and quantification according to the present invention is depicted.

The core method 10 for dynamic normalization for perfusion comparison and quantification is depicted in FIG. 3, embedded in further steps.

As described earlier, both the controlled acquisition 22 as well as the controlled injection 24 of contrast agent allows the acquisition of meaningful input data or coronary angiogram data.

Both the, optional, injection tip tracking 28 as well as the main collector tracking 30 allows the subsequent step of contrast agent integration 20. In particular, the main collector tracking 30 facilitates determining and monitoring the location where volume flow is to be estimated and followed with regard to time.

A subsequent cardiac DSA process 32 allows ultimately obtaining perfusion image information.

Method 10 according to the present invention comprises the contrast agent volume integration step 20 as well as the subsequent data normalization step 34, resulting in meaningful image information to allow a comparison or even quantification of perfusion image information.

The step of contrast agent volume integration 20 comprises the individual sub-steps of determining or estimating the total volume flow in the main collector 20a. Further, a contrast flow measurement 20b is performed, so providing all required parameters for the subsequent integration over time 21.

Calibration step 20c is necessary to estimate relative normalization $Q'_T(t)$. However, to determine absolute normalization $Q_T(t)$, both a from calibration and the absolute total volume flow $q_T(t)$ are required. For obtaining absolute normalization $Q_T(t)$, the 3D vessel geometry and the acquisition geometry, i.e. knowledge about the vessel in 3D and the way this vessel is projected onto the 2D plane, are required as well. Without those values, only $q'_T(t)$ may be estimated, and therefore only $Q'_1(t)$.

The vessel geometry may be obtained from a 3D data acquisition, pre- or peri-interventional, and from vessel segmentation in 3D. The acquisition geometry may be acquired from the system. In addition, in order to analyse the observed contrast in the DSA in an absolute way, it may be required to register the 3D data to the considered 2D projection. A typical example is a vessel segment tilted in space and projected in the angiogram image with a certain degree of forshortening. The 3D vessel geometry provides the diameter of the vessels and its tilted angle in space. It is subsequently assumed that this vessel segment is precisely the feeding point (i.e. the main collector). If correctly registered with the angiogram, this observed main collector in the angiogram may be related to the 3D vessel segment. Knowing the 2D acquisition geometry, the foreshortening ratio between 3D and 2D may be deduced.

Now, because foreshortening creates more absorption because more contrast agent is crossed by the X-Ray beams through the tilted vessel and because the observed length of the vessel segment is reduced in the 2D projected as opposed to the 3D actual vessel length, a certain number of corrections should be involved to translate the observed volume flow in 2D into an actual volume flow in 3D. Typically, simply the forshortening ratio $\beta$, the inverse of the cosine of the angle between the 3D vessel segment and the 2D image plane, may be sufficient for such a correction. Indeed, the observed length is to be multiplied by $\beta$ to get the actual 3D length, with means that the estimated flow velocity in 2D should also be multiplied by $\beta$ to get the corresponding velocity in 3D. The same kind of reasoning typically holds true for the observed vessel section.

There is also an approximate $\beta$ factor between the observed 2D and the 3D vessel section. However, when 3D is available, the volume flow may be determined directly from the estimated velocity in 3D, that is $\beta$ times the velocity estimated in 2D, multiplied by the actual 3D section area.

In other words, for obtaining absolute total blood volume flow or absolute normalization, both calibration step 20c (for $\alpha$) also step 20d (for $\varphi$), relating to determining 3D vessel-geometry, determining 2D acquisition geometry and determining the relation in between, are required. Thus, the output of step 20c may be considered to be $\alpha$, while the output of step 20d may be considered to be $\varphi$.

Figure 4:
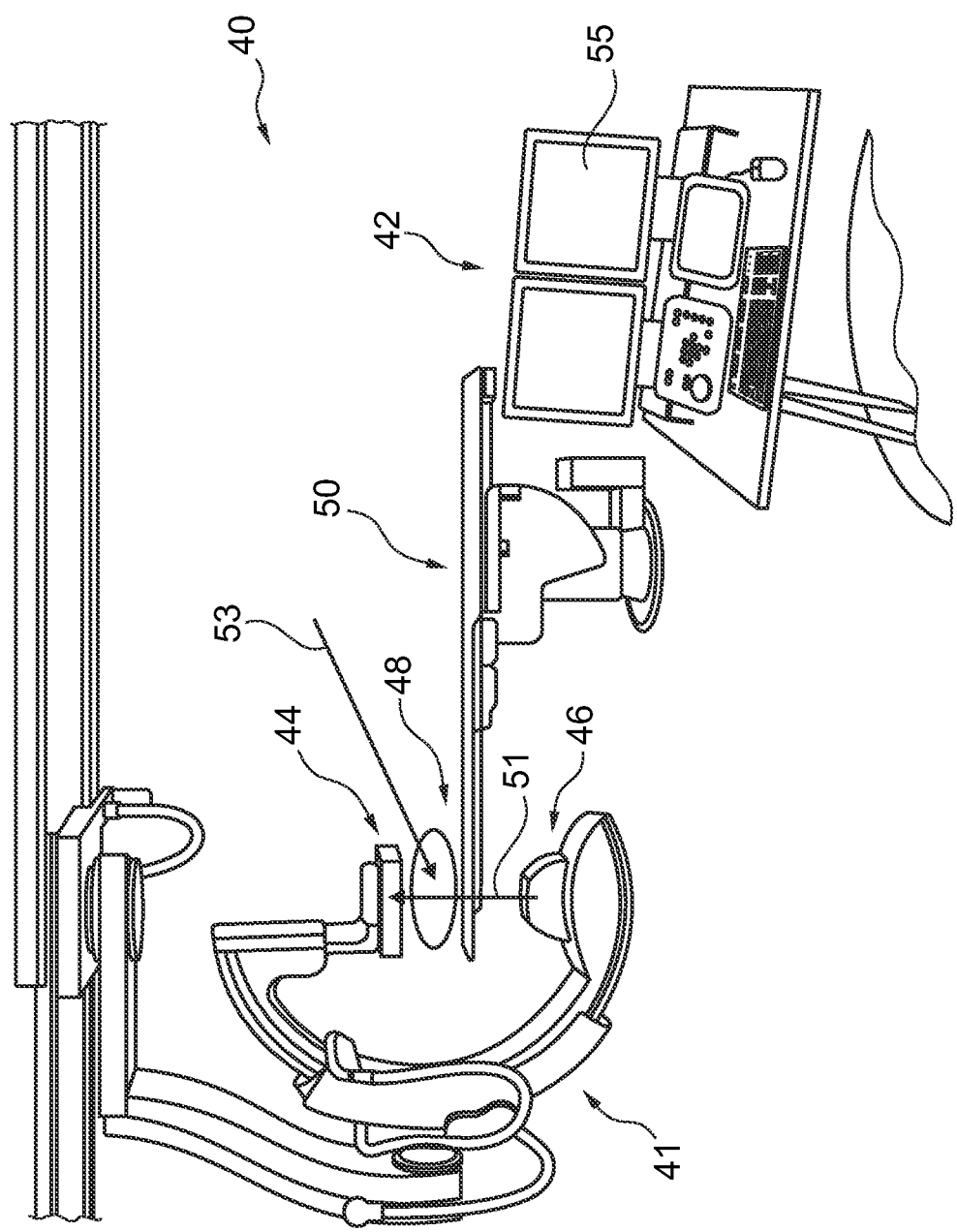
FIG. 4 shows an exemplary apparatus and x-ray imaging apparatus for dynamic normalization of perfusion data for comparison and quantification.

Now referring to FIG. 4, an exemplary x-ray imaging apparatus for dynamic normalization o image data for perfusion comparison and quantification, in particular cardiac perfusion imaging, is depicted.

FIG. 4 shows an x-ray imaging system 40, comprising an apparatus 42 for dynamic normalization of data for perfusion comparison and quantification.

X-ray imaging system 40 is exemplarily comprises a ceiling mounted C-arc 41 having an x-ray source 46 and an x-ray detector 44. An object 48 is situated on support 50 and is arrangeable in the path of X-radiation 51, emanating from the x-ray source, penetrating object 48 and subsequently arriving at x-ray detector 44 for acquisition of x-ray images of the internal structure of object 48.

An injection catheter system 53 is depicted schematically only, for applying contrast agent during a PCI procedure, for obtaining a coronary angiogram and subsequently myocardial perfusion image data.

Apparatus 42 may either employ pre-acquired angiogram image data for normalization or may employ life acquired x-ray image information from x-ray system 40.

Apparatus 42 is adapted for performing the method as depicted in FIG. 3, in particular either step of the cardiac DSA process 32, the contrast agent volume integration 20 with some or all of the associated steps 20*a,b,c*, 21 as well as data normalization 34.

For visualization, comparison or quantification, image information may be displayed to a user using visualization element 55. E.g. a side-by-side comparison of pre- and post-stenting image data may be performed using visualization element 55

Apparatus 42 may also provide absolute quantification data derived from the normalized perfusion image information to a user.

LIST OF REFERENCE SIGNS

2 Myocardium
4 Aorta
5 Bifurcation
6 Right coronary artery
7 Main collector
8 Left coronary artery
8*a* Circumflex artery
8*b* Left anterior descending artery
9 Coronary ostia
10 Method for dynamic normalization for perfusion comparison and quantification
20 STEP: Contrast agent volume integration
20*a* STEP: Volume flow estimation
20*b* STEP: Contrast measurement
20*c* STEP: Calibration
20*d* STEP: Determining 3D Vessel Geometry/2D Acquisition Geometry
21 STEP: Integration over time
22 STEP: Controlled acquisition
24 STEP: Controlled injection
26 STEP: Input data acquisition
28 STEP: Injection tip tracking
30 STEP: Main collector tracking
32 STEP: Cardiac DSA process
34 STEP: Data normalization
36 STEP: Quantification or comparison
40 x-ray system
41 C-arm
42 Apparatus
44 x-ray detector
46 x-ray source
48 Object
50 Support
51 X-radiation
53 Injection catheter
55 Visualization element

The invention claimed is:

1. An apparatus configured for perfusion assessment, comprising:
 a contrast agent injection device for injecting contrast agent in a blood vessel;
 a medical imaging device that acquires image data; and
 a processing device configured to:
 determine an integrated volume of contrast agent flowing through a defined section of blood vessel, wherein the integrated volume of contrast agent is determined by integrating volume flow in said defined section of said blood vessel over time as a function of a total volume flow in said defined section of said blood vessel and an average contrast observed over said defined section of said blood vessel, and wherein the total volume flow is determined by a locally arranged flowmeter within a main collector; and
 normalize the image data based on the determined integrated volume of contrast agent.

2. The apparatus of claim 1, further comprising a visualization element;
 and configured for, via said visualization element, visually providing, to a user, at least one of first normalized perfusion x-ray image data of a first image acquisition and second normalized perfusion x-ray image data of a second image acquisition.

3. The apparatus of claim 1, further comprising an x-ray source, and
 an x-ray detector,
 wherein an object, having a region of interest, is arrangeable between the x-ray source and the x-ray detector, and
 wherein the x-ray source and the x-ray detector are operatively coupled for acquisition of said perfusion data to be normalized, said perfusion data to be normalized being perfusion x-ray image data of said region of interest.

4. The apparatus of claim 1, said blood vessel being a coronary artery.

5. The apparatus of claim 1, wherein the normalizing is dynamically performed.

6. The apparatus of claim 1, wherein said assessment operates on said blood vessel, said blood vessel has a region into which said contrast agent is injected, said injecting is performed in an injection direction, the derived total volume flow is in said direction, and, with said injection device being disposed such that backflow of the injected contrast agent occurs in said blood vessel in a direction opposite to said injection direction, said determining of said amount entails determining a volume flow of the injected contrast agent over a defined cross-section of said region that is beyond a point at which said backflow occurs.

7. A method for dynamic normalization of image data for perfusion comparison and quantification, comprising the steps of:
 determining an integrated volume of contrast agent flowing through a defined section of blood vessel, wherein the integrated volume of contrast agent is determined by integrating volume flow in said defined section of said blood vessel over time as a function of a total volume flow in said defined section of said blood vessel and an average contrast amount observed over the defined section of said blood vessel; and wherein the total volume flow is determined by a locally arranged flowmeter within a main collector and,
 normalizing the image data based on the determined integrated volume of contrast agent.

8. The method according to claim 7, wherein the total volume flow is determined by estimating a total fluid flow in x-ray image information at the defined section of the blood vessel.

9. The method according to claim 7,
 wherein at least one of:
 a) an absolute integrated volume of contrast agent $Q_I(t)$ is determined by the equation $$Q_I(t) = \int_{t_0}^{t} q_I(t)\, dt = \frac{1}{\alpha} \cdot \int_{t_0}^{t} q_T(t) \cdot C(t)\, dt$$

and;
 b) a relative integrated volume of contrast agent $Q'_I(t)$ is determined by the equation $$Q'_I(t) = \int_{t_0}^{t} q'_T(t) \cdot C(t) dt$$

wherein $q_I(t)$ corresponds to an absolute volume flow of contrast agent at a defined section of the blood vessel;

wherein $q_T(t)$ corresponds to an absolute total volume flow at the defined section of the blood vessel; and wherein $q'_T(t)$ corresponds to a relative volume flow of contrast agent at the defined section of the blood vessel;

wherein $C(t)$ corresponds to observed average contrast over the defined section; and wherein $\alpha$ is a constant, t0 is a starting injection time, and t is a current time.

10. The method according to claim 9,
wherein at least one of:
absolute normalized perfusion data $D_n(t)$ is determined by the equation $$D_n(t) = \frac{D(t)}{Q_I(t)}$$

and;

relative normalized perfusion data $D'_n(t)$ is determined by the equation $$D'_n(t) = \frac{D(t)}{Q'_I(t)}$$

wherein $D(t)$ corresponds to imaged perfusion data that is in X-ray image data.

11. The method according to claim 7,
wherein at least one of:
a) the blood vessel is a representation of a blood vessel, in pre-acquired x-ray image data; and
b) the method is a method for image post-processing of pre-acquired x-ray image data.

12. The method of claim 7, said blood vessel having an ostium, said method further comprising the steps of:
placing a catheter tip at said ostium, thereby entering said blood vessel; and
injecting said contrast agent through the placed catheter tip.

13. The method of claim 12, said placing being such that backflow of the injected contrast agent occurs in said blood vessel, said determining being based on flow through a cross-section of said blood vessel disposed beyond said backflow.

14. A method for dynamic normalization of image data for perfusion comparison and quantification, comprising the steps of:
determining an integrated volume of contrast agent flowing through a defined section of a blood vessel, wherein the integrated volume of contrast agent is determined by integrating volume flow in said defined section of said blood vessel over time as a function of a total volume flow in the defined section of the blood vessel and an average contrast amount observed over the defined section of the blood vessel; and wherein the total volume flow is determined by a locally arranged flowmeter within a main collector and
normalizing the image data based on the a determined amount of contrast agent in the blood vessel.

15. The method of claim 14, said blood vessel having an ostium, said method further comprising the steps of:
placing a catheter tip at said ostium, thereby entering said blood vessel; and
injecting said contrast agent through the placed catheter tip.

16. The method of claim 15, said placing being such that backflow of the injected contrast agent occurs in said blood vessel, the integrating being based on flow through a cross-section of said blood vessel disposed beyond said backflow.

17. A non-transitory computer readable medium embodying a program for dynamic normalization of image data, said program having instructions executable by a processor for performing a plurality of acts, from among said plurality there being the acts of:
determining an integrated volume of contrast agent flowing through a defined section of a blood vessel, wherein the integrated volume of contrast agent is determined by integrating volume flow in said defined section of said blood vessel over time as a function of a total volume flow in the defined section of the blood vessel and an average contrast amount observed over the defined section of the blood vessel; and wherein the total volume flow is determined by a locally arranged flowmeter within a main collector and
normalizing the image data based on the determined integrated volume of contrast agent.

18. The computer readable medium of claim 17, said blood vessel having an ostium, among said plurality there being the further act of:
for a catheter tip that is placed at said ostium, thereby entering said blood vessel, injecting said contrast agent through the placed catheter tip.

19. The computer readable medium of claim 18, said placing being such that backflow of the injected contrast agent occurs in said blood vessel, said determining being based on flow through a cross-section of said blood vessel disposed beyond said backflow.

* * * * *